(12) United States Patent
Wilks et al.

(10) Patent No.: US 9,162,970 B2
(45) Date of Patent: Oct. 20, 2015

(54) PROMOTION OF IMINE FORMATIN VIA CATIONIC RESIN CATALYST

(71) Applicant: KELLOGG BROWN & ROOT LLC, Houston, TX (US)

(72) Inventors: Theodor Wilks, Houston, TX (US); Eric Wing-Tak Wong, Houston, TX (US); Matthew R. Ulrich, Katy, TX (US)

(73) Assignee: KELLOGG BROWN & ROOT LLC, Houston, TX (US)

( * ) Notice: Subject to any disclaimer, the term of this patent is extended or adjusted under 35 U.S.C. 154(b) by 0 days.

(21) Appl. No.: 14/632,265

(22) Filed: Feb. 26, 2015

(65) Prior Publication Data

US 2015/0251988 A1    Sep. 10, 2015

Related U.S. Application Data

(60) Provisional application No. 61/947,746, filed on Mar. 4, 2014.

(51) Int. Cl.
*C07C 209/36* (2006.01)
*C07C 209/84* (2006.01)
*B01J 19/24* (2006.01)

(52) U.S. Cl.
CPC ............... *C07C 209/84* (2013.01); *B01J 19/24* (2013.01); *C07C 209/36* (2013.01); *B01J 2219/24* (2013.01)

(58) Field of Classification Search
CPC .............................. C07C 209/36; C07C 209/84

USPC .................................................. 564/420, 437
See application file for complete search history.

(56) References Cited

U.S. PATENT DOCUMENTS

| 3,553,268 A | 1/1971 | Solomon et al. |
| 4,207,262 A * | 6/1980 | Graham et al. ............... 564/437 |
| 4,322,556 A | 3/1982 | Patterson et al. |
| 4,415,754 A | 11/1983 | Lawrence |
| 5,283,365 A | 2/1994 | Nagata et al. |
| 5,292,960 A | 3/1994 | Meier et al. |
| 5,616,806 A | 4/1997 | Nagata et al. |
| 7,091,381 B2 | 8/2006 | Suzuki et al. |
| 7,692,042 B2 | 4/2010 | Dugal et al. |
| 8,153,076 B2 | 4/2012 | Hassan et al. |
| 2007/0203364 A1 | 8/2007 | Dugal et al. |
| 2007/0238901 A1 | 10/2007 | Dugal et al. |
| 2010/0015019 A1 | 1/2010 | Hassan et al. |
| 2012/0172627 A1 | 7/2012 | Wong |

FOREIGN PATENT DOCUMENTS

CN    102911064 A    6/2013

* cited by examiner

*Primary Examiner* — Kamal Saeed
*Assistant Examiner* — Janet L Coppins
(74) *Attorney, Agent, or Firm* — Gary M. Machetta

(57) ABSTRACT

Methods and systems for purifying a crude aniline. The method can include contacting a crude aniline that can include aniline, water, and cyclohexanone with a cation exchange resin to produce a cyclohexanone-lean product that contains less cyclohexanone than the crude aniline. The cation exchange resin can be a solid, a semi-solid, or a combination thereof.

20 Claims, 4 Drawing Sheets

PROMOTION OF IMINE FORMATIN VIA CATIONIC RESIN CATALYST

CROSS-REFERENCE TO RELATED APPLICATION

This application claims priority to U.S. Provisional Patent Application No. 61/947,733, filed Mar. 4, 2014, which is incorporated by reference herein.

BACKGROUND

1. Field

Embodiments described generally relate to methods and systems for purifying a crude aniline. More particularly, the embodiments described relate to methods and systems for reducing a concentration of cyclohexanone in a crude aniline.

2. Description of the Related Art

Aromatic amines, including aniline, are precursors for the preparation of many industrial chemicals. The largest use of aniline is in the production of methylene diphenyl diisocyanate (MDI), which can be reacted with polyols to produce polyurethane. Aniline can be produced by a catalytic hydrogenation of nitrobenzene, as shown in Reaction 1.

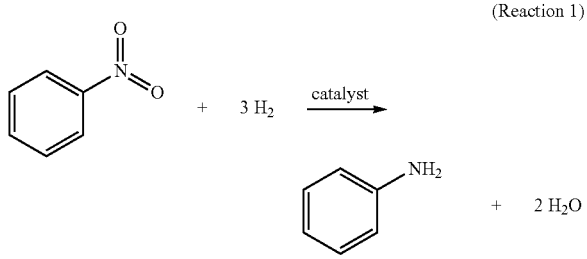

(Reaction 1)

The catalyst can include Raney nickel; palladium on charcoal or nickel; or cobalt, copper or nickel on kieselguhr. Reaction 1, however, can result in the formation of impurities. One such impurity is cyclohexanone, which is difficult to remove from aniline by physical methods. For example, aniline and cyclohexanone cannot be readily separated by distillation because of their similarity in boiling points.

The crude aniline containing the cyclohexanone can be reacted under acidic conditions to form an imine compound, or Schiff's Base, namely cyclohexylidene aniline, as shown in Reaction 2.

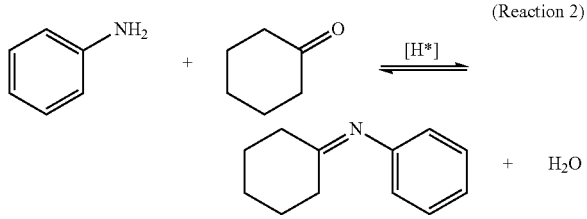

(Reaction 2)

The aniline can then be purified by removing the higher molecular weight cyclohexylidene aniline. The reaction conditions for Reaction 2, however, are susceptible to upsets in upstream equipment and process conditions, which can result in an off-specification product.

There is a need, therefore, for improved methods and systems for purifying a crude aniline.

DETAILED DESCRIPTION

Methods and systems for purifying a crude aniline are provided. The method can include contacting a crude aniline that can include aniline, water, and cyclohexanone with a cation exchange resin to produce a cyclohexanone-lean product that contains less cyclohexanone than the crude aniline. The cation exchange resin can be a solid, a semi-solid, or a combination thereof.

It has been surprisingly and unexpectedly discovered that by using heterogeneous reaction conditions for Reaction 2, where a cationic resin catalyst or cationic exchange resin is used to provide an acidic environment, a concentration of cyclohexanone in an aniline feed or "crude aniline" can be significantly reduced by reacting the cyclohexanone with the aniline to produce cyclohexylidene aniline. The acidic nature of the cationic exchange resin can catalyze the reaction without consuming the cation. The cation exchange resin can reduce the concentration of cyclohexanone in the crude aniline by at least 10%, at least 20%, at least 30%, at least 50%, at least 70%, or at least 90%. For example, the crude aniline can be contacted with the cationic exchange resin to produce a cyclohexanone-lean product or purified aniline product that has a concentration of cyclohexanone reduced by about 30%, about 40%, or about 50% to about 70%, about 80%, about 90%, or about 95% or more, as compared to the crude aniline prior to contact with the cationic exchange resin. In another example, the cation exchange resin can reduce the concentration of cyclohexanone in the crude aniline by about 10% to about 50%, about 20% to about 50%, about 30% to about 60%, about 40% to about 65%, about 50% to about 70%, about 50% to about 75%, about 60% to about 90%. In another example, the cation exchange resin can reduce the concentration of cyclohexanone by at least 70%, at least 80%, at least 90%, or 95% in a crude aniline that contains about 100 ppmw to about 15,000 ppmw of cyclohexanone.

It has also been surprisingly and unexpectedly discovered that the cation exchange resin can reduce the concentration of cyclohexanone in the crude aniline by at least 20%, at least 30%, at least 40%, at least 50%, at least 60%, at least 70%, at least 80%, at least 90%, or at least 95% in a time period of less than 60 minutes, less than 45 minutes, less than 30 minutes, or less than 15 minutes. For example, the cation exchange resin can reduce the concentration of cyclohexanone in the crude aniline by at least 20%, at least 30%, at least 40%, at least 50%, at least 60%, at least 70%, at least 80%, at least 90%, or at least 95% in a time period of about 1 minute to about 15 minutes, about 5 minutes to about 20 minutes, about 15 minutes to about 30 minutes, about 25 minutes to about 40 minutes, about 35 minutes to about 50 minutes, or about 40 minutes to about 60 minutes.

Figure 1:
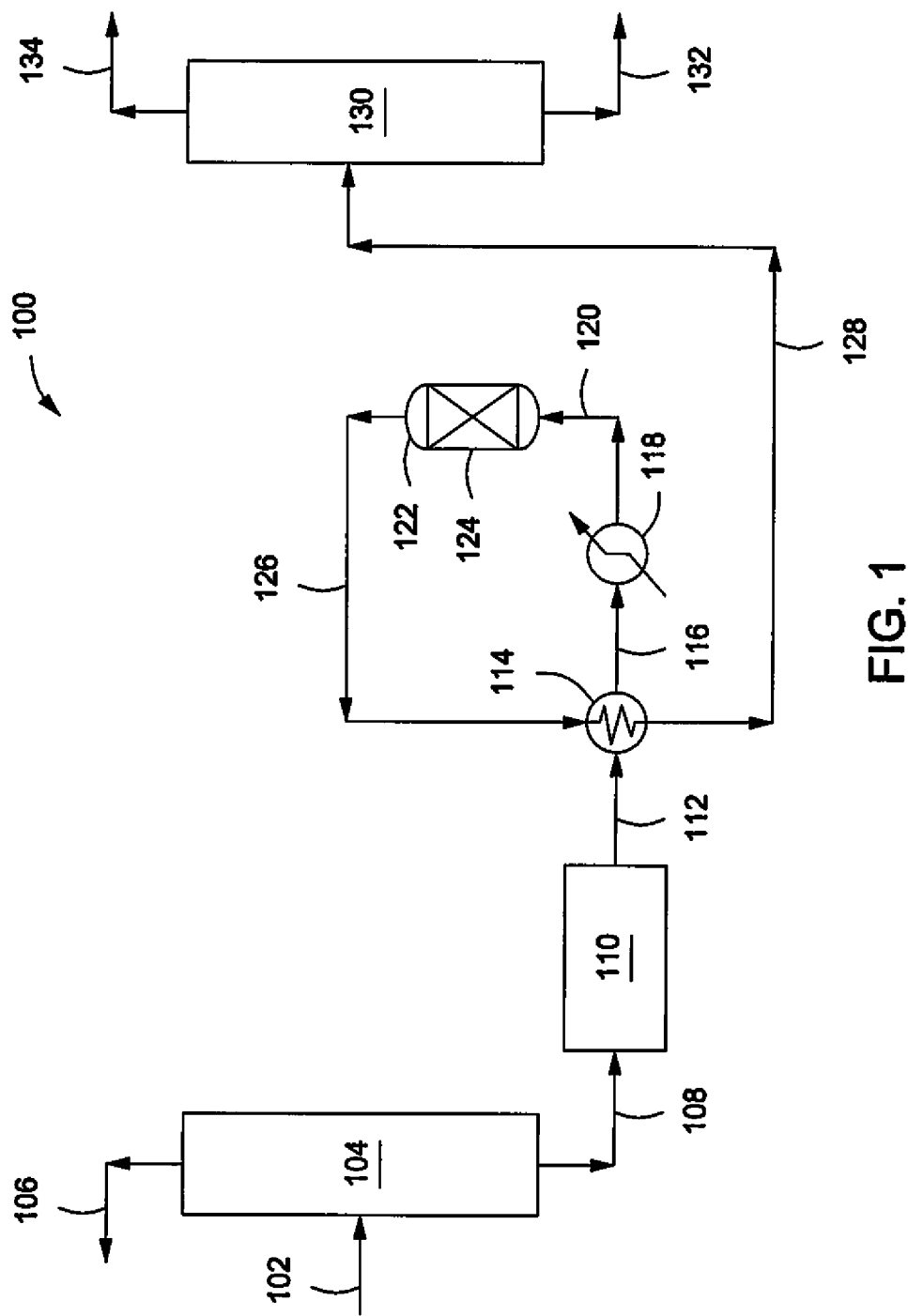
FIG. 1 depicts a schematic of an illustrative purification system for producing a purified aniline product from crude aniline that includes a reactor upstream of a cation exchange resin unit, according to one or more embodiments described.

FIG. 1 depicts a schematic of an illustrative purification system 100 for producing a purified aniline product 134 from crude aniline 102 that includes a reactor 110 upstream of a cation exchange resin unit 122. The system can include, but is not limited to, one or more dehydration units, e.g., one or more dehydration columns, 104, one or more cyclohexanone reduction reactors 110, one or more heat exchangers (two are shown 114, 118, one or more cation exchange resin units 122, and one or more separators, e.g., one or more distillation columns 130. The reactor 110 can be operated at a homogenous reaction condition. Crude aniline via line 102 can be introduced to the dehydration unit 104 to produce a dehydrated crude aniline via line 108 and a water containing overhead via line 106. The crude aniline in line 102 can include, but is not limited to, aniline, water, mononitrobenzene, cyclohexanone, toluene, benzene, cyclohexanol, phenol, toluidine, methylcyclopentane, methylcyclohexane, cyclohexylamine, one or more amines, one or more ketones, or any mixture thereof.

The crude aniline in line 102 can have a concentration of aniline from a low of about 85 wt %, about 88 wt %, or about 92 wt % to a high of about 95 wt %, about 97 wt %, or about 99 wt %. The crude aniline in line 102 can have a concentration of water from a low of about 1 wt %, about 3 wt %, or about 5 wt % to a high of about 8 wt %, about 12 wt %, or about 15 wt %. The crude aniline in line 102 can have a concentration of cyclohexanone from a low of about 100 parts per million by weight ("ppmw"), about 250 ppmw, about 500 ppmw about 1,000 ppmw, or about 1,500 ppmw to a high of about 4,000 ppmw, about 6,000 ppmw, about 8,000 ppmw, or about 10,000 ppmw. The crude aniline in line 102 can have a total concentration of other impurities, which can include, but are not limited to, benzene, toluene, phenol, mononitrobenzene, toluidine, cyclohexanol, cyclohexylamine, methylcyclopentane, methylcyclohexane, and/or cyclohexylidene aniline, from a low of about 100 ppmw, about 250 ppmw, about 500 ppmw, about 750 ppmw, or about 1,000 ppmw to a high of about 1,250 ppmw, about 1,500 ppmw, about 1,750 ppmw, or about 10,000 ppmw.

The dehydration unit 104 can separate at least a portion of water and/or other impurities from the aniline to produce the dehydrated crude aniline via line 108 and the water containing overhead via line 106. The water containing overhead in line 106 can include, but is not limited to, water, toluene, benzene, cyclohexanol, phenol, methylcyclopentane, methylcyclohexane, cyclohexanone, cyclohexylamine, or any mixture thereof. The dehydration unit 104 can include any system, device, or combination of systems and/or devices capable of separating at least a portion of any water contained in the crude aniline introduced thereto via line 102. For example, the dehydration unit 104 can be or include one or more distillation columns or fractionation columns. The dehydration unit 104 can be operated at a temperature of at least about 100° C. and up to about 215° C., which can vaporize at least a portion of the water and at least a portion of one or more other impurities such as toluene, benzene, cyclohexanol, phenol, methylcyclopentane, methylcyclohexane, cyclohexanone, and/or cyclohexylamine having a boiling point less than the temperature within the dehydration unit 104.

The dehydration unit 104 can be empty, partially filled, or completely filled with one or more materials to improve mass transfer and/or separation of the water from the crude aniline. For example, the fill material can include, but is not limited to, structured materials, random packed materials, trays, or any combination thereof. Two or more types of fill material can be disposed within the dehydration unit 104. For example, the dehydration unit 104 can contain random dumped packing, one or more trays, or a combination thereof.

Illustrative trays can include, but are not limited to perforated trays, sieve trays, bubble cap trays, floating valve trays, fixed valve trays, tunnel trays, cartridge trays, dual flow trays, cartridge trays, snap-in valve trays, chimney trays, slit trays, or any combination thereof. As used herein, the term "packing material" can include, but is not limited one or more types of structured and/or random shaped material disposed within the dehydration unit 104. The packing material can increase the effective surface area within the dehydration unit 104, which can improve the mass transfer between liquid and/or gas phases within the dehydration unit 104. The packing material can be made of any suitable metallic materials. Illustrative examples of random packing material can include, but are not limited to, Raschig rings, Lessing rings, I-rings, saddle rings, Intalox saddles, Tellerettes, Pall rings, U-rings, or any combination thereof. Illustrative examples of commercially available structured packing can include, but are not limited to, structured packing, corrugated sheets, crimped sheets, gauzes, grids, wire mesh, monolith honeycomb structures, or any combination thereof.

The dehydrated crude aniline via line 108 can have a concentration of aniline from a low of about 98 wt %, about 98.5 wt %, or about 99 wt % to a high of about 99.5 wt %, about 99.9 wt %, or about 99.99 wt %. The dehydrated crude aniline via line 108 can have a concentration of water from a low of about 10 ppmw, about 100 ppmw, or about 200 ppmw to a high of about 1,000 ppmw, about 3,000 ppmw, or about 5,000 ppmw. The dehydrated crude aniline in line 108 can have a concentration of cyclohexanone from a low of about 100 ppmw, about 250 ppmw, about 500 ppmw, about 750 ppmw, or about 1,000 ppmw to a high of about 2,000 ppmw, about 3,000 ppmw, about 4,000 ppmw, or about 5,000 ppmw. The dehydrated crude aniline in line 108 can have a total concentration of other impurities that can include, but are not limited to, benzene, toluene, mononitrobenzene, phenol, toluidine, cyclohexanol, cyclohexylamine, methylcyclopentane, methylcyclohexane, and/or cyclohexylidene aniline, from a low of about 50 ppmw, about 100 ppmw, about 500 ppmw about 750 ppmw, or about 1,000 ppmw to a high of about 2,500 ppmw, about 3,500 ppmw, about 4,250 ppmw, or about 5,000 ppmw.

The dehydrated crude aniline via line 108 can be introduced to and reacted in the reactor 110 to produce a cyclohexanone-reduced product via line 112 that contains less cyclohexanone as compared to the dehydrated crude aniline in line 108. The reactor 110 can be a homogenous reactor where a portion of the cyclohexanone can react within the reactor 110 to produce an imine compound, e.g., cyclohexylidene aniline, as shown in Reaction 2. For example, the cyclohexanone can react with an amine, $R-NH_2$ in the presence of a catalyst, e.g., sulfuric acid, to reduce the cyclohexanone concentration in the dehydrated crude aniline. For example, the concentration of the cyclohexanone in the dehydrated crude aniline can be reduced in an amount from a low of about 10%, and 20%, about 30%, or about 40% to a high of about 50%, about 60%, about 70%, about 80%, or about 90%.

The cyclohexanone-reduced product in line 112 can have a concentration of aniline from a low of about 98 wt %, about 98.5 wt %, or about 99 wt % to a high of about 99.9 wt %, about 99.95 wt %, or about 99.99 wt %. The cyclohexanone-reduced product in line 112 can have a concentration of water from a low of about 10 ppmw, about 100 ppmw, or about 200 ppmw to a high of about 1,000 ppmw, about 3,000 ppmw, or about 5,000 ppmw. The cyclohexanone-reduced product in line 112 can have a concentration cyclohexanone from a low of about 10 ppmw, about 50 ppmw, about 100 ppmw, about 300 ppmw, or about 500 ppmw to a high of about 1,000 ppmw, about 1,500 ppmw, about 2,000 ppmw, about 2,500 ppmw, or about 3,000 ppmw. The cyclohexanone-reduced product in line 112 can have a concentration of cyclohexylidene aniline from a low of about 50 ppmw, about 100 ppmw, about 500 ppmw about 750 ppmw, or about 1,000 ppmw to a high of about 2,500 ppmw, about 3,500 ppmw, about 4,250 ppmw, or about 5,000 ppmw. The cyclohexanone-reduced product in line 112 can have a total concentration of other impurities that can include, but are not limited to, benzene, toluene, phenol, mononitrobenzene, toluidine, cyclohexanol, cyclohexylamine, methylcyclopentane, and/or methylcyclohexane, from a low of about 50 ppmw, about 100 ppmw, about 500 ppmw about 750 ppmw, or about 1,000 ppmw to a high of about 2,500 ppmw, about 3,500 ppmw, about 4,250 ppmw, or about 5,000 ppmw.

The cyclohexanone-reduced product in line 112 can be introduced to the one or more heat exchangers 114, 118. The first heat exchanger 114 and the second heat exchanger 118 can be or include one or more shell-and-tube, plate and frame, spiral wound, U-tube, bayonet style heat exchangers, or any combination thereof. The first heat exchanger 114 can cool the cyclohexanone-reduced product via line 112 recovered from the reactor 110 to produce a first cooled cyclohexanone-reduced product via line 116.

The second heat exchanger 118 can cool the first cooled cyclohexanone-reduced product in line 116 to produce a second cooled cyclohexanone-reduced product via line 120. The second cooled cyclohexanone-reduced product in line 120 can be at a pressure of about 300 kPa, or about 500 kPa to about 1,000 kPa, about 1,500 kPa, or about 2,000 kPa. The second cooled cyclohexanone-reduced product in line 120 can be at a temperature from a low of about 50° C., about 70° C., or about 90° C. to a high of about 110° C., about 130° C., or about 150° C.

Heat can be indirectly transferred from the reaction product to one or more heat transfer mediums in the first and second heat exchangers 114, 118 to produce the first and second cooled cyclohexanone-reduced products via lines 116, 120, respectively, and heated heat transfer mediums from the first and second heat exchangers 114, 118. Illustrative heat transfer mediums can include, but are not limited to, cooling water, boiler feed water, low pressure steam, medium pressure steam, glycols, a cyclohexanone-lean product, air and/or other gaseous fluids, or any mixture thereof. The cyclohexanone-reduced product via line 112 can be cooled by direct contact or mixing (not shown) with a cooling fluid such as water to produce the cooled reaction product via lines 116, 120. The cyclohexanone-reduced product via line 112 can be cooled by a combination of indirect heat exchange and direct contact cooling.

The cooled cyclohexanone-reduced product via line 120 can be introduced to the cation exchange resin unit 122 to produce a cyclohexanone-lean product via line 126. The cation exchange resin unit 122 can include one more cation exchange resin beds 124. The cation exchange resin bed 124 can include any one or more cation exchange resins that can catalyze the conversion of the cyclohexanone molecule to an imine, namely cyclohexylidene aniline, as shown in Reaction 2. The cation exchange resin can include one or more $H^+$ functional groups, sulfuric acid, $HSO_4^-$ functional groups, or any mixture or combination thereof. The cation ionic exchange resins can include, but are not limited to, one or more of the AMBERLYST® ion exchange resins available from Dow Water & Process Solution, one or more of the PUROLITE® series ion exchange resins available from the Purolite Company, one or more of the LEWATIT® series ion exchange resins available from the Lanxess Corp., or any mixture thereof. For example, the cation exchange resin can be or include a polymer based on a cross-linked styrene divinylbenzene copolymer, which can contain sulfonic acid groups. For example, the cation exchange resin can include, but is not limited to, AMBERLYST® 36, PUROLITE® CT-151, LEWATIT® K2629, or any mixture thereof.

The cation exchange resin can be solid, semi-solid, or a combination of solid and semi-solid structures. For example, the cation exchange resin can be in the form of solid particles, semi-solid particles, e.g., a gelled particle, or a mixture thereof. The cation exchange resin can be or include macroporous particles, microporous particles, or a mixture thereof. The solid cation exchange resin can be in the form of pellets, beads, granules, flakes, spheres, cubes, blocks, fibers, filaments, threads, or any mixture thereof. As used herein, the terms "semi-solid" and "semi-solid particle" refer to a three-dimensional structure that itself is insoluble in a particular liquid. The three-dimensional structure can be capable of absorbing and retaining a quantity of the liquid to form a stable, often soft and pliable structure. The cation exchange resin can be solid and/or semi-solid structures disposed within a fixed bed, a fluid or moving bed, or a combination thereof. In another example, the solid and/or semi-solid structures can be supported on one or more support members such as a rigid support member, between two or more support members such as screens, plates, and the like, or any combination thereof.

The cation exchange resin disposed within a fixed bed can have a bed depth from a low of about 5 cm, about 10 cm, about 20 cm, about 30 cm, or about 40 cm to a high of about 70 cm, about 85 cm, about 100 cm, about 150 cm, about 200 cm, or about 300 cm. For example, the cation exchange resin can be disposed within a fixed bed having a bed depth of about 40 cm to about 80 cm, about 50 cm to about 70 cm, about 60 cm to about 120 cm, about 60 cm to about 200 cm, or about 90 cm to about 250 cm. The fixed bed containing the cation exchange resin can be disposed within the cation exchange resin unit 122. The cation exchange resin unit 122 can contain or otherwise include one, two, four, six, eight, ten, twelve, fifteen, twenty, or more discrete or separate fixed beds. Any number of cation exchange resin units each having any number of fixed beds disposed therein can be arranged in series, parallel, or both with respect to one another. The number of fixed beds, the size of the fixed beds, and the particular cation exchange resin disposed within each fixed bed can be the same or different between any two cation exchange resin units.

The average cross-sectional size or length of the ion exchange material, e.g., ion exchange resins, can be at a low of about 0.01 mm, about 0.05 mm, about 0.1 mm, about 0.3 mm, or about 0.5 mm to a high of about 1 mm, about 2 mm, about 3 mm, about 5 mm, about 7 mm, about 9 mm, about 11 mm, about 13 mm, about 15 mm, or about 20 mm. The ion exchange material, e.g., ion exchange resins, can have an average pore diameter from a low of about 20 angstroms (Å), about 50 Å, or about 100 Å to a high of about 200 Å, about 300 Å, about 400 Å, or about 500 Å. For example, the cation exchange resin can have an average pore diameter of about 200 Å to about 400 Å, or about 150 Å to about 300 Å, or about 225 Å to about 450 Å. The ion exchange material, e.g., ion exchange resins, can have a pore volume from a low of about 0.05 mL/g, about 0.1 mL/g, or about 0.15 mL/g to a high of about 0.3 mL/g, about 0.5 mL/g, or about 1 mL/g. For example, the cation exchange resin can have a pore volume about 0.15 mL/g to about 0.25 mL/g, about 0.2 mL/g to about 0.4 mL/g, or about 0.2 mL/g to about 1 mL/g. The ion exchange material, e.g., ion exchange resins, can have a surface area from a low of about 10 m$^2$/g, about 15 m$^2$/g, or about 20 m$^2$/g to a high of about 30 m$^2$/g, about 40 m$^2$/g, or about 50 m$^2$/g.

Depending, at least in part, on the particular cation exchange resin and/or the amount of cyclohexanone present, the crude aniline in line 108, the cyclohexanone-reduced product in line 112, the first cooled cyclohexanone-reduced product in line 116, and/or the second cooled cyclohexanone-reduced product in line 120 can be contacted with the cation exchange resin at a rate of about 0.1 m$^3$ crude aniline product per 1 m$^3$ of the cation exchange resin per hour to about 35 m$^3$ crude product per 1 m$^3$ of the cation exchange resin per hour. For example, the crude aniline in line 108, the cyclohexanone-reduced product in line 112, the first cooled cyclohexanone-reduced product in line 116, and/or the second cooled cyclohexanone-reduced product in line 120 can be contacted with the cation exchange resin at a rate of about 1 m$^3$, about 3 m$^3$, about 5 m$^3$, or about 10 m$^3$ to a high of about 15 m$^3$, about 20 m$^3$, about 25 m$^3$, or about 30 m$^3$ crude product per 1 m$^3$ of the cation exchange resin per hour. In another example, the crude aniline in line 108, the cyclohexanone-reduced product in line 112, the first cooled cyclohexanone-reduced product in line 116, and/or the second cooled cyclohexanone-reduced product in line 120 can be contacted with the cation exchange resin at a rate from about 1 m$^3$ to about 8 m$^3$ crude product per 1 m$^3$ cation exchange resin per hour, from about 2 m$^3$ to about 4 m$^3$ crude product per 1 m$^3$ cation exchange resin per hour, from about 3 m$^3$ to about 5 m$^3$ crude product per 1 m$^3$ cation exchange resin per hour, about 4 m$^3$ to about 6 m$^3$ crude product per 1 m$^3$ cation exchange resin per hour, about 10 m$^3$ to about 27 m$^3$ crude product per 1 m$^3$ cation exchange resin per hour. The cation exchange resin can remain in the solid or semi-solid form upon and after contact with the crude aniline in line 108, the cyclohexanone-reduced product in line 112, the first cooled cyclohexanone-reduced product in line 116, and/or the second cooled cyclohexanone-reduced product in line 120.

Depending, at least in part, on the particular ion exchange material, the crude aniline in line 102, the dehydrated crude aniline in line 108, the cyclohexanone-reduced product in line 112, the first cooled cyclohexanone-reduced product in line 116, and/or the second cooled cyclohexanone-reduced product in line 120 can be introduced to the cation exchange resin unit 122 and contacted with the cation exchange resin at a temperature from a low of about 50° C., about 60° C., or about 70° C. to a high of about 80° C., about 90° C., about 100° C., about 110° C., about 120° C., about 130° C., about 140° C., about 150° C., or about 155° C. Depending, at least in part, on the particular cation exchange resin, the crude aniline in line 102, the dehydrated crude aniline in line 108, the cyclohexanone-reduced product in line 112, the first cooled cyclohexanone-reduced product in line 116, and/or the second cooled cyclohexanone-reduced product in line 120 can be at a pressure from a low of about 101 kPa, about 200 kPa, or about 500 kPa to a high of about 1,000 kPa, about 1,200 kPa, or about 2,000 kPa when contacted therewith.

When the capacity of the cation exchange resin nears exhaustion, e.g., the cation exchange resin no longer reacts with a sufficient amount of cyclohexanone present in the crude aniline, the cation exchange resin can be replaced with a new ion exchange material. When the capacity of the cation exchange resin nears exhaustion, the cation exchange resin can be regenerated. For example, contacting the crude aniline with the cation exchange resin can be stopped or diverted elsewhere, e.g., another location containing another cation exchange resin and one or more regenerate materials can be contacted with the exhausted cation exchange resin to produce a regenerated cation exchange resin that can again be contacted with the crude aniline in line 102, the dehydrated crude aniline in line 108, the cyclohexanone-reduced product in line 112, the first cooled cyclohexanone-reduced product in line 116, and/or the second cooled cyclohexanone-reduced product in line 120.

The cation exchange resin unit 122 can be or include a vessel having an ion exchange material, such as the cation exchange resin contained therein. The vessel of the cation exchange resin unit 122 can have a plurality of shapes including, but not limited to, a cube, a rectangular box, a cylinder, a triangular prism, a hyperboloid structure, or some other shape or combination thereof. For example, the vessel can be cylindrical having a longitudinal axis that can be horizontally oriented or oriented at an angle with respect to horizontal of between about 1°, about 5°, about 10°, about 20°, or about 30° and about 60°, about 70°, or about 80°. The vessel can also have a longitudinal axis that can be vertically oriented or oriented at an angle with respect to vertical of between about 1°, about 5°, about 10°, about 20°, or about 30° and about 60°, about 70°, or about 80°. The cation exchange resin unit 122 or a longitudinal axis of the cation exchange resin unit 122 can be at least substantially horizontally oriented. The cation exchange resin unit 122 or a longitudinal axis of the cation exchange resin unit 122 can be at least substantially vertically oriented. As used herein, the term "substantially vertical" refers to about −5° to about 5°, about −3° to about 3°, about −2° to about 2°, about −1° to about 1°, about −0.1° to about 0.1°, or about −0.0001° to about 0.0001° with respect to vertical.

The cyclohexanone-lean product in line 126 can have a concentration of aniline from a low of about 98 wt %, about 98.5 wt %, or about 99 wt % to a high of about 99.9 wt, about 99.95 wt %, or about 99.99 wt %. The cyclohexanone-lean product in line 126 can have a concentration of water from a low of about 10 ppmw, about 100 ppmw, or about 200 ppmw to a high of about 1,000 ppmw, about 3,000 ppmw, or about 5,000 ppmw. The cyclohexanone-lean product in line 126 can have a concentration cyclohexanone from a low of about 1 ppmw, about 10 ppmw, about 25 ppmw, or about 40 ppmw to a high of about 60 ppmw, about 70 ppmw, about 85 ppmw, or about 100 ppmw. For example, the cyclohexanone-lean product via line 126 can have a cyclohexanone concentration of less than 150 ppmw, less than 100 ppmw, less than 50 ppmw, less than 40 ppmw, less than 30 ppmw, less than 20 ppmw, or less than 10 ppmw. The cyclohexanone-lean product in line 126 can have a concentration of cyclohexylidene aniline from a low of about 50 ppmw, about 100 ppmw, about 500 ppmw about 750 ppmw, or about 1,000 ppmw to a high of about 2,500 ppmw, about 3,500 ppmw, about 4,250 ppmw, or about 5,000 ppmw. The cyclohexanone-lean product in line 126 can have a total concentration of other impurities that can include, but are not limited to, benzene, toluene, phenol, mononitrobenzene, cyclohexanol, toluidine, cyclohexylamine, methylcyclopentane, and/or methylcyclohexane, from a low of about 50 ppmw, about 100 ppmw, about 500 ppmw about 750 ppmw, or about 1,000 ppmw to a high of about 2,500 ppmw, about 3,500 ppmw, about 4,250 ppmw, or about 5,000 ppmw.

At least a portion of the cyclohexanone-lean product in line 126 can act as a heat transfer medium to cool the cyclohexanone-reduced product entering the first heat exchanger 114 to produce the first cooled cyclohexanone-reduced product via line 116 and a heated cyclohexanone-lean product via line 128. Optionally, the cyclohexanone-lean product in line 126 can byass the first heat exchanger 114. The heated cyclohexanone-lean product in line 128 can be at a pressure from a low of about 101 kPa, about 300 kPa, or about 500 kPa to a high of about 1,000 kPa, about 1,500 kPa, or about 2,000 kPa. The heated cyclohexanone-lean product in line 128 can be at a temperature from a low of about 100° C., about 110° C., about 120° C., or about 130° C. to a high of about 150° C., about 170° C., or about 200° C.

The cyclohexanone-lean product via line 126 and/or the heated cyclohexanone-lean product in line 128 can be separated, e.g., via distillation, in the separator 130 to separate impurities and produce a purified aromatic amine product. For example, the cyclohexanone-lean product via line 126 and/or the heated cyclohexanone-lean product in line 128 can be separated in the separator 130 to produce a final or purified aniline product via line 134 and impurities comprising a waste or heavies byproduct via line 132. The impurities separated from the purified aniline as waste via line 132 can include any compounds and/or components other than aniline. Illustrative impurities can include, but are not limited to, imine compounds, mononitrobenzene, toluidine, phenol, or any mixture thereof.

The purified aniline product in line 134 can have a concentration of aniline from a low about 99 wt % to a high of about 99.99 wt %. The purified aniline product in line 134 can have a concentration of aniline of at least 99 wt %, at least 99.4 wt %, or at least 99.5 wt % to about 99.9 wt % or about 99.95 wt %. The purified aniline product in line 134 can have a concentration of cyclohexanone from a low about 1 ppmw, about 5 ppmw, about 10 ppmw, about 15 ppmw, about 20 ppmw, or about 30 ppmw to a high of about 50 ppmw, about 65 ppmw, about 75 ppmw, about 85 ppmw, or about 100 ppmw. The purified aniline product in line 134 can have a concentration of water from a low about 10 ppmw about 50 ppmw, about 100 ppmw, about 500 ppmw about 750 ppmw, or about 1,000 ppmw to a high of about 2,500 ppmw, about 3,500 ppmw, about 4,250 ppmw, or about 5,000 ppmw. The purified aniline product in line 134 can have a concentration of cyclohexylidene aniline from a low of about 1 ppmw, about 5 ppmw, about 10 ppmw, about 15 ppmw, about 20 ppmw, or about 30 ppmw to a high of about 50 ppmw, about 65 ppmw, about 75 ppmw, about 85 ppmw, or about 100 ppmw. The purified aniline product in line 134 can have a total concentration of other impurities that can include, but are not limited to, benzene, toluene, phenol, cyclohexanol, cyclohexylamine, mononitrobenzene, toluidine, methylcyclopentane, and/or methylcyclohexane, from a low of about 50 ppmw, about 100 ppmw, about 200 ppmw, or about 300 ppmw to a high of about 500 ppmw, about 750 ppmw, or about 1,000 ppmw.

The separator 130 can be similar to the dehydration unit 104. For example, the separator 130 can include any system, device, or combination of systems and/or devices capable of separating at least a portion of the impurities from the aniline in the dehydrated product introduced thereto via line 128. For example, the separator 130 can be or include one or more distillation columns or fractionation columns. The separator 130 can be empty, partially filled, or completely filled with one or more trays and/or packing material to improve mass transfer and/or separation of the aniline from the dehydrated product.

The system for producing the purified aniline product can include the dehydration unit 104 configured to receive crude aniline via line 102 and to produce the dehydrated crude aniline. The dehydrated crude aniline can be recovered via one or more lines 108 coupled to or in fluid communication with the dehydration unit 104 and coupled to or in fluid communication with the reactor 110 to produce the cyclohexanone-reduced product. The first heat exchanger 114 can cool the cyclohexanone-reduced product via line 112 to produce a first cooled the cyclohexanone-reduced product that can be recovered via one or more lines 116 coupled to or in fluid communication with the first heat exchanger 114 and a second heat exchanger 118. The second heat exchanger 118 can further cool the first cooled the cyclohexanone-reduced product via line 216 recovered from the first heat exchanger 114 to produce the second cooled the cyclohexanone-reduced product that can be recovered via 120.

The second cooled cyclohexanone-reduced product via line 120 can be introduced to the one or more cation exchange resin units 122 to produce a cyclohexanone-lean product. The cation exchange resin unit 122 can include one more cation exchange resins 124 as discussed and described above. The cyclohexanone-lean product can be recovered via one or more lines 126 coupled to or in fluid communication with the cation exchange resin unit 122 and coupled to or in fluid communication with the first heat exchanger 114. The cyclohexanone-lean product can act as a heat transfer medium to cool the cyclohexanone-reduced product entering the first heat exchanger 114 to produce the first cooled cyclohexanone-reduced product via line 116 and a heated cyclohexanone-lean product that can be recovered via one or more lines 128 coupled to or in fluid communication with the first heat exchanger 114 and one or more separators 130. The dehydration unit 104, the first heat exchanger 114, the second heat exchanger 118, the cation exchange resin unit 122, the reactor 110, and the separator 130 can be as discussed and described above or elsewhere herein.

The cyclohexanone-lean product via line 212 can be distilled or separated in the separator 130 to produce a final or purified aniline product via line 234 and a waste or heavies byproduct via line 232. The purified aniline product via line 234 and the waste via line 232 can be as discussed and described above and elsewhere herein.

Figure 2:
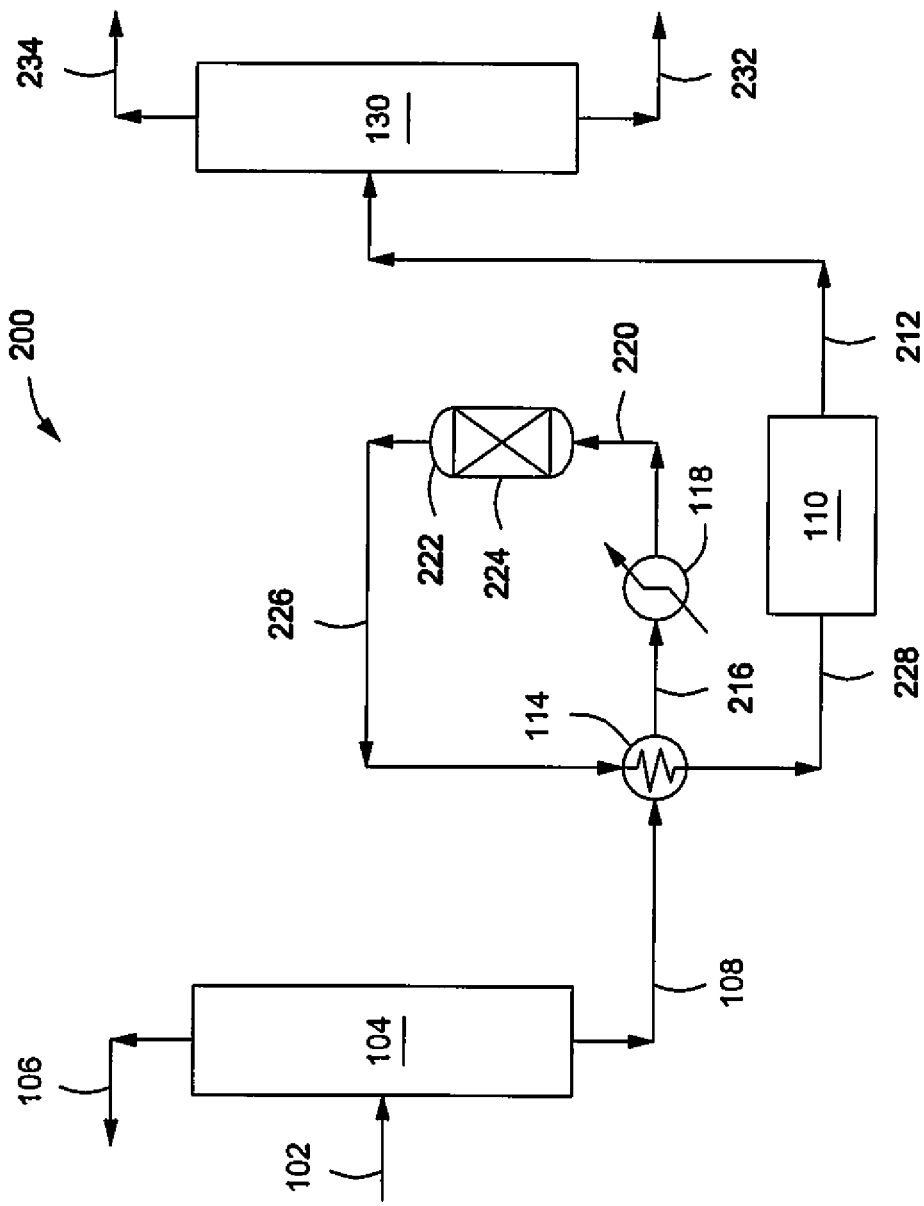
FIG. 2 depicts a schematic of another illustrative purification system for producing a purified aniline product from crude aniline that includes a reactor downstream of a cation exchange resin unit, according to one or more embodiments described.

FIG. 2 depicts a schematic of another illustrative purification system 200 for producing a purified aniline product 234 from a crude aniline 102 that includes a reactor 110 downstream of a cation exchange resin unit 222. The purification system 200 can include one or more dehydration units 104, one or more heat exchangers 114, 118, one or more cation exchange resin units 222, one or more reactors 110, one or more separators 130, or any combination thereof. The dehydrated crude aniline in line 108 can be introduced to the heat exchanger 114 to produce a first cooled dehydrated crude aniline via line 216.

The first cooled dehydrated crude aniline in line 216 can be introduced to the second heat exchanger 118 to produce a second cooled dehydrated crude aniline via line 220. The second cooled dehydrated crude aniline in line 220 can be at a temperature from a low of about 50° C., about 75° C., or about 100° C. to a high of about 115° C., about 130° C., or about 150° C. The second cooled dehydrated crude aniline in line 220 can be at a pressure from a low of about 300 kPa, about 500 kPa, about 750 kPa, or about 1,000 kPa to about a high of about 1,250 kPa, about 1,500 kPa, about 1,750 kPa, or about 2,000 kPa.

The second cooled dehydrated crude aniline in line 220 can have the same or similar composition as the dehydrated crude aniline in line 108 discussed and described above with reference to FIG. 1. The second cooled dehydrated crude aniline in line 220 can be introduced to the cation exchange resin unit 222 to produce a cyclohexanone-reduced product via line

226. The cation exchange resin unit 222 can include one more cation exchange resin beds 124 and one or more cation exchange resins therein. The cation exchange resin unit 222 can be the same as or similar to the cation exchange resin unit 122 discussed and described above with reference to FIG. 1.

The cyclohexanone-reduced product in line 226 can include aniline, water, mononitrobenzene, phenol, toluidine, cyclohexanone, toluene, benzene, cyclohexanol, methylcyclopentane, methylcyclohexane, cyclohexylamine, one or more amines, one or more ketones, or any mixture thereof. The cyclohexanone-reduced product in line 226 can have a concentration of aniline from a low of about 98 wt %, about 98.3 wt %, or about 98.5 wt % to a high of about 98.7 wt %, about 98.9 wt %, or about 99 wt %. The cyclohexanone-reduced product in line 226 can have a concentration of water from a low of about 10 ppmw, about 50 ppmw, about 100 ppmw, about 500 ppmw about 750 ppmw, or about 1,000 ppmw to a high of about 2,500 ppmw, about 3,500 ppmw, about 4,250 ppmw, or about 5,000 ppmw. The cyclohexanone-reduced product in line 226 can have a concentration of cyclohexanone from a low of about 10 ppmw, about 50 ppmw, about 100 ppmw, about 250 ppmw, about 500 ppmw, or about 750 ppmw to a high of about 1,250 ppmw, about 1,750 ppmw, about 2,250 ppmw, about 2,600 ppmw, or about 3,000 ppmw. The cyclohexanone-reduced product in line 226 can have a concentration of cyclohexylidene aniline from a low of about 50 ppmw, about 100 ppmw, about 500 ppmw about 750 ppmw, or about 1,000 ppmw to a high of about 2,500 ppmw, about 3,500 ppmw, about 4,250 ppmw, or about 5,000 ppmw. The cyclohexanone-reduced product in line 226 can have a total concentration of other impurities that can include, but are not limited to, benzene, toluene, phenol, mononitrobenzene, toluidine, cyclohexanol, cyclohexylamine, methylcyclopentane, and/or methylcyclohexane, from a low of about 50 ppmw, about 100 ppmw, about 500 ppmw about 750 ppmw, or about 1,000 ppmw to a high of about 2,500 ppmw, about 3,500 ppmw, about 4,250 ppmw, or about 5,000 ppmw.

The cyclohexanone-reduced product in line 226 can be heated in one or more heat exchangers 114 to produce a heated cyclohexanone-reduced product via line 228. The cyclohexanone-reduced product in line 226 can act as a heat transfer medium to cool the dehydrated crude aniline entering the first heat exchanger 114 to produce the first cooled dehydrated crude aniline via line 216 and the heated cyclohexanone-reduced product via line 228. In another example, the cyclohexanone-reduced product in line 226 can be heated in a third heat exchanger (not shown). The third heat exchanger can be similar to or the same as the second heat exchanger 118 discussed and described above. In another example, the cyclohexanone-reduced product in line 226 can be introduced directly to the reactor 110 without first being heated in any heat exchanger.

The heated cyclohexanone-reduced product via line 228 can be introduced to the reactor 110 to produce a cyclohexanone-lean product via line 212. The heated cyclohexanone-reduced product can be reacted in the reactor 110 to remove at least a portion of any cyclohexanone present. The amount of cyclohexanone removed from the heated cyclohexanone-reduced product in the reactor 110 can be from a low of about 30%, about 40%, or about 50% to a high of about 60%, about 70%, about 80%, or about 90%. The cyclohexanone-lean product in line 212 can be at a temperature form a low of about 150° C., about 155° C., or about 160° C. to a high of about 163° C., about 166° C., or about 170° C. and a pressure from a low of about 101 kPa, about 120 kPa, or about 140 kPa to a high of about 160 kPa, about 180 kPa, or about 200 kPa.

The cyclohexanone-lean product via line 212 can have a concentration of aniline from a low of about 98 wt %, about 98.5 wt %, or about 99 wt % to a high of about 99.5 wt %, about 99.9 wt %, about 99.95 wt %, or about 99.99 wt %. The cyclohexanone-lean product via line 212 can have a concentration of water from a low of about 10 ppmw about 50 ppmw, about 100 ppmw, about 500 ppmw about 750 ppmw, or about 1,000 ppmw to a high of about 2,500 ppmw, about 3,500 ppmw, about 4,250 ppmw, or about 5,000 ppmw. The cyclohexanone-lean product via line 212 can have a concentration of cyclohexanone from a low of about 1 ppmw, about 5 ppmw, about 10 ppmw, or about 20 ppmw to a high of about 40 ppmw, about 60 ppmw, about 80 ppmw, or about 100 ppmw. The cyclohexanone-lean product via line 212 can have a concentration of cyclohexylidene aniline from a low of about 50 ppmw, about 100 ppmw, about 500 ppmw about 750 ppmw, or about 1,000 ppmw to a high of about 2,500 ppmw, about 3,500 ppmw, about 4,250 ppmw, or about 5,000 ppmw. The cyclohexanone-lean product in line 212 can have a total concentration of other impurities that can include, but are not limited to, benzene, toluene, phenol, mononitrobenzene, cyclohexanol, toluidine, cyclohexylamine, methylcyclopentane, and/or methylcyclohexane, from a low of about 50 ppmw, about 100 ppmw, about 500 ppmw about 750 ppmw, or about 1,000 ppmw to a high of about 2,500 ppmw, about 3,500 ppmw, about 4,250 ppmw, or about 5,000 ppmw.

The cyclohexanone-lean product via line 212 can be distilled or otherwise separated in the separator 130 to produce a final or purified aniline product via line 234 and a waste or heavies byproduct via line 232. The purified aniline product in line 234 can have a concentration of aniline from a low about 99 wt %, about 99.3 wt %, or about 99.5 wt % to a high of about 99.9 wt %, about 99.95 wt %, or about 99.99 wt %. The purified aniline product in line 234 can have a concentration of aniline of at least 99 wt %, at least 99.4 wt %, or at least 99.5 wt % to about 99.9 wt % or about 99.95 wt %. The purified aniline product in line 234 can have a concentration of cyclohexanone from a low of about 1 ppmw, about 5 ppmw, about, about 10 ppmw, or about 20 ppmw to a high of about 40 ppmw, about 60 ppmw, about 80 ppmw, or about 100 ppmw. The purified aniline product in line 234 can have a concentration of water from a low about 10 ppmw, about 50 ppmw, about 100 ppmw, about 500 ppmw about 750 ppmw, or about 1,000 ppmw to a high of about 2,500 ppmw, about 3,500 ppmw, about 4,250 ppmw, or about 5,000 ppmw. The purified aniline product in line 234 can have a concentration of cyclohexylidene aniline from a low of about 1 ppmw, about 5 ppmw, about, about 10 ppmw, or about 20 ppmw to a high of about 40 ppmw, about 60 ppmw, about 80 ppmw, or about 100 ppmw. The purified aniline product in line 234 can have a total concentration of other impurities that can include, but are not limited to, benzene, toluene, phenol, cyclohexanol, cyclohexylamine, mononitrobenzene, toluidine, methylcyclopentane, and/or methylcyclohexane, from a low of about 50 ppmw, about 100 ppmw, about 500 ppmw about 750 ppmw, or about 1,000 ppmw to a high of about 2,500 ppmw, about 3,500 ppmw, about 4,250 ppmw, or about 5,000 ppmw.

Figure 3:
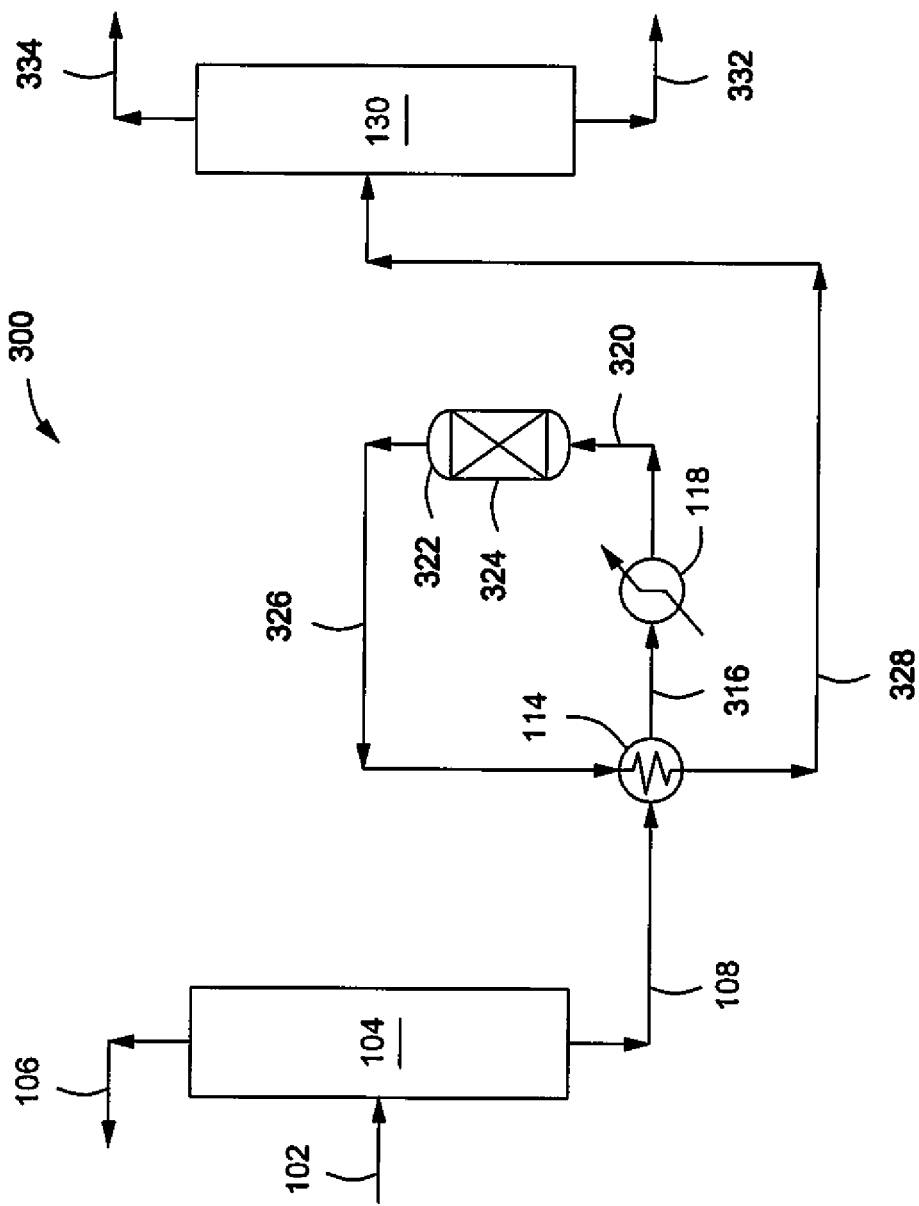
FIG. 3 depicts a schematic of another illustrative purification system for producing a purified aniline product from crude aniline that does not include a reactor upstream or downstream of a cation exchange resin unit, according to one or more embodiments described.

FIG. 3 depicts a schematic of another illustrative purification system 300 for producing a purified aniline product 334 from crude aniline 102 that does not include a reactor upstream or downstream of a cation exchange resin unit 322. One or more lines 102 containing crude aniline can be coupled to or in fluid communication with one or more dehydration units (one is shown 104), which can separate at least a portion of any remaining water and/or other impurities contained therein to produce a dehydrated crude aniline. The dehydrated crude aniline can be recovered via one or more lines 108 coupled to or in fluid communication with the dehydration unit 104 and coupled to or in fluid communication with a first heat exchanger 114.

The dehydrated crude aniline in line 108 can have the same or similar composition as the dehydrated crude anilines 108 discussed and described above with reference to FIGS. 1 and/or 2. The first heat exchanger 114 can cool the dehydrated crude aniline via line 108 to produce a first cooled dehydrated crude aniline that can be recovered via one or more lines 316 coupled to or in fluid communication with the first heat exchanger 114 and a second heat exchanger 118. The second heat exchanger 118 can further cool the first cooled dehydrated crude aniline via line 316 recovered from the first heat exchanger 114 to produce a second cooled dehydrated crude aniline that can be recovered via 320.

The second cooled dehydrated crude aniline via line 320 can be introduced to one or more cation exchange resin units 322 to produce a cyclohexanone-lean product via line 326. The cation exchange resin unit 322 can include one more cation exchange resins 324. The cation exchange resin unit 322 and the cation exchange resin 324 can be the same or similar to the cation exchange resin units 122 and/or 222 and the cation exchange resins 124 and/or 224, respectively, as discussed and described above with reference to FIGS. 1 and 2. The cyclohexanone-lean product in line 326 can have compositions similar to the compositions of the cyclohexanone-lean product in line 126 discussed and described above with reference to FIG. 1. In one example, the cyclohexanone-lean product in line 326 can have the same composition as the cyclohexanone-lean product in line 126 discussed and described above with reference to FIG. 1.

The cyclohexanone-lean product in line 326 can be used as a heat transfer medium to cool the dehydrated crude aniline introduced via line 108 to the first heat exchanger 114 to produce the first cooled dehydrated crude aniline via line 316 and a heated cyclohexanone-lean product that can be recovered via one or more lines 328 coupled to or in fluid communication with one or more separators 130. The dehydration unit 104, the first heat exchanger 114, the second heat exchanger 118, the cation exchange resin unit 322, and the separator 130 can be as discussed and described above or elsewhere herein.

The heated cyclohexanone-lean product via line 328 can be distilled or otherwise separated in the separator 130 to produce a final or purified aniline product via line 334 and a waste or heavies byproduct via line 332. The purified aniline product via line 334 and the waste via line 332 can be as discussed and described above and elsewhere herein.

The purified aniline product in line 334 can have a concentration of aniline from a low about 99 wt %, about 99.3 wt % or about 99.5 wt % to a high of about 99.9 wt %, about 99.95 wt %, or about 99.99 wt %. The purified aniline product in line 334 can have a concentration of aniline of at least 99 wt %, at least 99.4 wt %, or at least 99.5 wt % to about 99.9 wt %, or about 99.95 wt %. The purified aniline product in line 334 can have a concentration of cyclohexanone from a low about 1 ppmw, about 5 ppmw, about, about 10 ppmw, or about 20 ppmw to a high of about 40 ppmw, about 60 ppmw, about 80 ppmw, or about 100 ppmw. The purified aniline product in line 334 can have a concentration of water from a low about 10 ppmw, about 50 ppmw, about 100 ppmw, about 500 ppmw about 750 ppmw, or about 1,000 ppmw to a high of about 2,500 ppmw, about 3,500 ppmw, about 4,250 ppmw, or about 5,000 ppmw. The purified aniline product in line 334 can have a concentration of cyclohexylidene aniline from a low of about 1 ppmw, about 5 ppmw, about, about 10 ppmw, or about 20 ppmw to a high of about 40 ppmw, about 60 ppmw, about 80 ppmw, or about 100 ppmw. The purified aniline product in line 334 can have a total concentration of other impurities that can include, but are not limited to, benzene, toluene, phenol, cyclohexanol, cyclohexylamine, mononitrobenzene, toluidine, methylcyclopentane, and/or methylcyclohexane, from a low of about 50 ppmw, about 100 ppmw, about 200 ppmw, or about 300 ppmw to a high of about 500 ppmw, about 750 ppmw, or about 1,000 ppmw.

Figure 4:
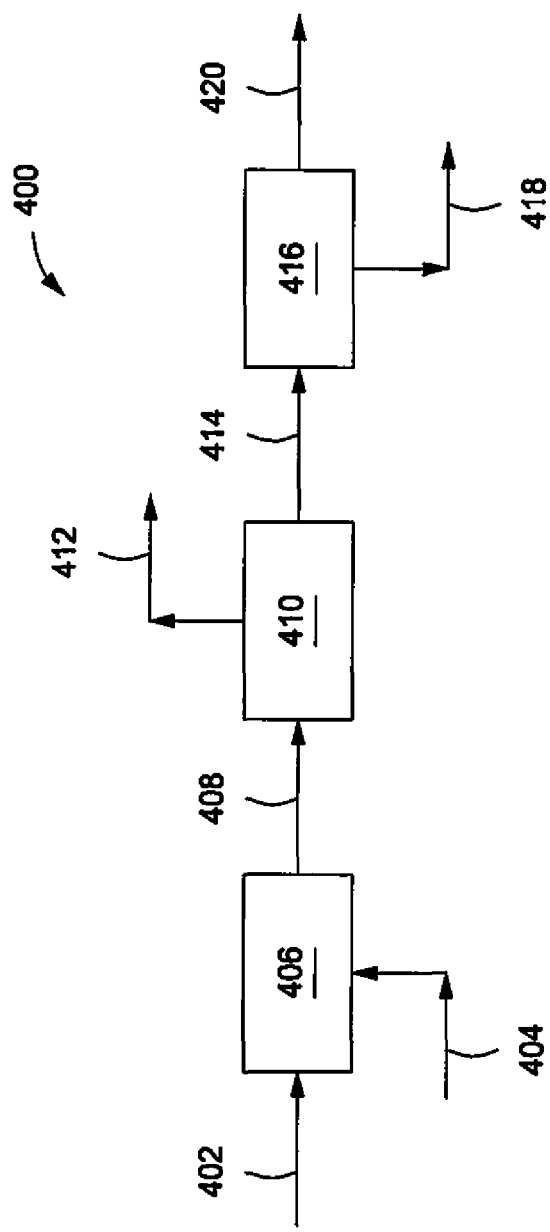
FIG. 4 depicts a schematic of an illustrative system for producing aniline and separating impurities therefrom, according to one or more embodiments described.

FIG. 4 depicts a schematic of an illustrative system 400 for producing aniline and separating impurities therefrom. The system 400 can include one or more hydrogenation reactors 406, one or more phase separators 410, and one or more purification systems 416. The one or more purification systems 416 can be as discussed and described above with reference to FIGS. 1-3. For example, the one or more purification systems 416 can be or include one or more of purification systems, 100, 200, and/or 300.

In operation, one or more aromatic nitro compounds via line 402 and hydrogen via line 404 can be introduced to the hydrogenation reactor 406 to produce a raw aniline product via line 408. The composition of the raw aniline product in line 408 can depend, at least in part, on the particular aromatic nitro compound or combination of aromatic nitro compounds that were hydrogenated. Illustrative aromatic nitro compounds can include, but are not limited to, nitrobenzene, nitrotoluene, dinitrotoluene (DNT), dinitrobenzene (DNB), or any mixture thereof. The raw aniline product or reaction product in line 408, before further purification or processing, can include a mixture of aniline and one or more impurities. Illustrative impurities can include, but are not limited to, water, phenol, nitrobenzene, benzene, nitrotoluene, dinitrotoluene (DNT), dinitrobenzene (DNB), polynitrobenzenes, methylcyclopentane, methylcyclohexane, mononitrotoluenes, nitroxylenes, cyclohexanone, cyclohexanol, cyclohexylamine, cyclohexanone, cyclohexylaniline, diphenylamines, phenylene diamines, cyclohexylidene aniline, toluidenes, xylidenes, toluene, or any mixture thereof.

The reaction product via line 408 can be a gas, a liquid, or a mixture thereof. The water and/or aniline, can also be introduced to the hydrogenation reactor 406 (not shown). The water can act as a quench fluid or medium that can be used to regulate or otherwise adjust a temperature within the hydrogenation reactor 406. The aniline can be used as a carrier fluid for one or more catalysts. As such, the aniline can also include one or more catalysts therein. In another example (not shown), the one or more catalysts can be introduced with the water and aniline. A byproduct or waste product (not shown) can also be recovered from the hydrogenation reactor 406. The byproduct or waste product can be a gas, liquid, or mixture thereof. The byproduct can include water, used, spent, or depleted catalyst, unreacted aromatic nitro compound(s), phenol, impurities, aniline, or any mixture thereof.

The hydrogenation or reduction of the aromatic nitro compound(s) in the hydrogenation reactor 406 can be carried out in a continuous, semi-continuous, and/or batch-wise manner. The hydrogenation of the aniline can be carried out under liquid phase conditions and/or gas phase conditions. The hydrogenation can be carried out at a temperature from a low of about 30° C., about 50° C., or about 80° C. to a high of about 250° C., about 300° C., about 400° C., or about 500° C. The hydrogenation can be carried out at a pressure from a low of about 101 kPa, about 150 kPa, or about 200 kPa to a high of about 1,000 kPa, about 2,000 kPa, about 3,500 kPa, or about 5,000 kPa. The reaction mixture of the aromatic nitro compound(s) can have a residence time during the hydrogenation from about 1 minute to about three hours. The molar ratio of hydrogen to the aromatic nitro compounds can have a low of about 3:1, about 3.2:1, or about 3.4:1 to a high of about 3.8:1, about 4:1, or about 4.2:1.

The hydrogenation of the aromatic nitro compound(s) can be carried out in the presence of one or more catalysts. Any suitable catalyst capable of promoting the hydrogenation of the aromatic nitro compound(s) can be used. Illustrative catalysts can include, but are not limited to, nickel, iron, chromium, platinum, copper, cobalt, palladium, rhodium, iridium, oxides thereof, hydroxides thereof, carbonates thereof, formates thereof, or any mixture thereof. The catalyst(s) can be unsupported or supported. Illustrative support materials can include, but are not limited to, carbon, aluminum oxide, and the like. The concentration of catalyst on a support can be at a low of about 0.1 wt % to about 50 wt %, based on the weight of the support material. The support material can have a particle size from about 0.01 μm to about 100 μm. The support material can have a surface area from about 10 m$^2$ to about 1,000 m$^2$ per gram.

In addition to the one or more catalysts, the hydrogenation of the aromatic nitro compound(s) can be carried out in the presence of water and/or aniline. The water and/or aniline can provide at least some control over the temperature of the hydrogenation reaction and/or to can facilitate introduction of the catalyst. For example, the catalyst can be introduced with a carrier fluid, e.g., aniline and/or water, to a hydrogenation reactor or hydrogenation zone. Used, spent, and/or depleted catalyst can be recovered from the hydrogenation reactor or zone as a byproduct or waste product.

The aromatic nitro compound(s) and an aniline/catalyst mixture can be introduced to the hydrogenation reactor 406 at a weight ratio from about 1:0.45 to about 1:0.6, about 1:0.5 to about 1:0.6, about 1:0.5 to about 1:0.55, or about 1:0.45 to about 1:0.55. The aromatic nitro compound(s) and the water can be introduced to the hydrogenation reactor 406 at a weight ratio from about 1:0.9 to about 1:1.25, about 1:1 to about 1:1.15, about 1:0.95 to about 1:1.1, or about 1:1 to about 1:1.1. The aromatic nitro compound(s) and hydrogen can be introduced to the hydrogenation reactor 406 at a weight ratio from about 30:1 to about 10:1, about 25:1 to about 10:1, about 20:1 to about 10:1, about 15:1 to about 10:1, or about 25:1 to about 12.5:1. The aromatic nitro compound(s) and an aniline/catalyst mixture can be at a weight ratio from about 1:0.5 to about 1:0.55, the aromatic nitro compound(s) and water can be at a weight ratio of about 1:1 to about 1:1.1, and the aromatic nitro compound(s) and hydrogen can be at a weight ratio of about 12.5:1 to about 25:1.

Illustrative processes for producing aniline can include those discussed and described in U.S. Pat. Nos. 8,809,587, 7,049,471 and 7,692,042 and U.S. Patent Application Publication Nos. 2007/0203364, 2007/0238901, and 2009/0065347.

The aniline can be produced by reacting one or more phenols with an amination agent. Illustrative phenols can include, but are not limited to, phenol, 2-methylphenol, 3-methylphenol, 4-methylphenol, o-, m- or p-isomers of ethylphenol and/or isopropylphenol, and alkyl phenols having at least one alkyl substituent, such as dimethylphenol, methylethylphenol, methylisopropylphenol, methylbutylphenol, diethylphenol, ethylbutylphenol, diisopropylphenol, isopropylbutylphenol, dibutylphenol, or any mixture thereof. Illustrative amination agents can include, but are not limited to, ammonia, ammonium carbonate, ammonium sulfate, ethylamine, n-propylamine, dimethylamine, diethylamine, diisopropylamine, methylethylamine, cyclohexylamine, aminopyridine, aniline, methylaniline, ethylaniline, n-propylaniline, isopropylaniline, dimethylaniline, diethylaniline, dipropylaniline, methylethylaniline, methylpropylanlline, or any mixture thereof. An illustrative processes for reacting one or more phenols with one or more amination agents can include the processes discussed and described in U.S. Pat. No. 5,545,753.

The reaction product via line 408 can have a concentration of aniline from about 15 wt % to about 80 wt %. For example, the amount of aniline in the reaction product via line 408 can be from a low of about 20 wt %, about 25 wt %, about 35 wt %, or about 45 wt % to a high of about 60 wt %, about 65 wt %, about 70 wt %, or about 75 wt %. The reaction product via line 408 can have a concentration of water from about 25 wt % to about 85 wt %. For example, the amount of water in the reaction product via line 408 can be a low of about 25 wt %, about 40 wt %, about 45 wt %, or about 50 wt % to a high of about 60 wt %, about 65 wt %, about 70 wt %, or about 75 wt %. The reaction product via line 408 can include about 35 wt % to about 45 wt % aniline and about 55 wt % to about 65 wt % water, and less than about 5 wt % other components.

The reaction product via line 408 can be cooled to produce a cooled reaction product. For example, heat from the reaction product can be indirectly transferred to a heat transfer medium to produce the cooled reaction product and a heated heat transfer medium. Illustrative heat transfer mediums can include, but are not limited to, cooling water, boiler feed water, low pressure steam, medium pressure steam, glycols, air and/or other gaseous fluids, or any mixture thereof. In another example, the reaction product can be cooled by direct contact or mixing with a cooling fluid such as water to produce the cooled reaction product. The reaction product via line 408 can be cooled by a combination of indirect heat exchange and direct contact cooling.

The cooled reaction product via line 408 can be at a temperature from a low of about 0° C., about 25° C., about 50° C., or about 75° C. to a high of about 150° C., about 175° C., or about 200° C. The cooled reaction product via line 408 can be at a pressure of a low of about 101 kPa, about 300 kPa, or about 500 kPa to a high of about 1,000 kPa, about 1,500 kPa, or about 2,000 kPa.

The cooled reaction product via line 408 can be introduced to the phase separator 410 to separate water via line 412 therefrom to produce a crude product or crude aniline via line 414. The crude aniline 414 can be or include the crude aniline via lines 102 as discussed and described above with reference to FIGS. 1-3 and elsewhere herein. A purified aniline product via line 420 and a waste via line 418 can be obtained from the one or more purification systems 416. The purified aniline product via line 420 and the waste via line 418 can be as discussed and described above and elsewhere herein. For example, the purified aniline product via line 420 can be or include the purified aniline product via lines 134, 234, and 334 and the waste via line 418 can be or include the waste via lines 132, 232, and 332. Additional details of aniline production and purification systems can be found in U.S. Patent Publication No. 2012/0172627 or U.S. Pat. No. 8,809,587.

EXAMPLES

To provide a better understanding of the foregoing discussion, the following non-limiting examples are provided. All parts, proportions and percentages are by weight unless otherwise indicated.

Example 1

A set of tests was conducted to determine the effect of the cation resins on Reaction 2. Two types of cation resins were tested, namely, a Type 13 (Ex. 1) and a Type 14 (Ex. 2) resin. The cation resins were used wet, same as shipping conditions, without prior drying. The Type 13 resin had an upper operating temperature of about 120° C. and the Type 14 resin had an upper operating temperature of about 150° C. The aniline used in the tests was reagent grade aniline that had a moisture content of less than 1,000 ppmw. About 50 mL of aniline was added to separate glass flasks and about 0.5 g of cation resin was added to each flask. The aniline/resin mixture was heated to reaction temperature and stirred on a shaker table. To each aniline/resin mixture, about 0.15 mL of reagent grade cyclohexanone was added to make up an aniline solution that contained about 3,000 ppmw of cyclohexanone. Samples were taken at 15 minutes, 30 minutes, and 60 minutes and analyzed for cyclohexanone content by gas chromatography. One control example (C1) was also tested that did not contain any cation exchange resin. The test conditions and results are shown in Table 1 below.

TABLE 1

| Example | Resin Type | Resin Quantity (g) | Bath Temp (° C.) | 15 min GC Results (ppmw) | 30 min GC Results (ppmw) | 60 min GC Results (ppmw) |
|---|---|---|---|---|---|---|
| C1 | None | None | 110 | 2,998 | 2,999 | 2,995 |
| Ex. 1 | 13 | 0.5 | 110 | 2,372 | 1,708 | 1,256 |
| Ex. 2 | 14 | 0.5 | 110 | 1,648 | 1,238 | 1,098 |

As shown in Table 1, when the aniline feeds that contained cyclohexanone were contacted with the cation exchange resins at a temperature of about 110° C. the concentration of cyclohexanone was significantly reduced. For example, after 60 minutes the concentration of cyclohexanone in Example 1 was reduced by about 58% and the concentration of cyclohexanone in Example 2 was reduced by about 63%. In contrast, the control example C1 contained about 2,995 ppmw cyclohexanone after 60 minutes.

Example 2

A second set of tests was conducted with solutions that had an initial concentration of about 1,000 ppmw of cyclohexanone in aniline were prepared. About 50 mL aniline and about 0.05 mL cyclohexanone were mixed with one another. About 0.5 g of the cation exchange resins (Type 13 and Type 14) were added to the aniline and cyclohexanone mixtures. The test conditions and results are shown in Table 2 below.

TABLE 2

| Example | Resin Type | Resin Quantity (g) | Bath Temp (° C.) | 15 min GC Results (ppmw) | 30 min GC Results (ppmw) | 60 min GC Results (ppmw) |
|---|---|---|---|---|---|---|
| Ex. 3 | 13 | 0.5 | 110 | 868 | 713 | 475 |
| Ex. 4 | 14 | 0.5 | 110 | 724 | 396 | 148 |

As shown in Table 2, when the aniline feeds that contained cyclohexanone were contacted with the cation exchange resins at a temperature of about 110° C. and the concentration of cyclohexanone was significantly reduced. For example, after about 60 minutes the concentration of cyclohexanone was reduced by about 52.5% and about 85.2% for Examples 3 and 4, respectively.

Example 3

A third set of tests was conducted with mixtures that had an initial concentration of about 1,000 ppmw of cyclohexanone in aniline were prepared. About 50 mL aniline and about 0.05 mL cyclohexanone were mixed with one another. About 1 g of the cation exchange resins (Type 13 and Type 14) were added to the aniline and cyclohexanone mixtures. The test conditions and results are shown in Table 3 below.

TABLE 3

| Example | Resin Type | Resin Quantity (g) | Bath Temp (° C.) | 15 min GC Results (ppmw) | 30 min GC Results (ppmw) | 60 min GC Results (ppmw) |
|---|---|---|---|---|---|---|
| Ex. 5 | 13 | 1 | 110 | 843 | 726 | 479 |
| Ex. 6 | 14 | 1 | 110 | 561 | 391 | 360 |

As shown in Table 3, when the aniline feeds that contained cyclohexanone were contacted with the cation exchange resins at a temperature of about 110° C. the concentration of cyclohexanone was significantly reduced. For example, after about 60 minutes the concentration of cyclohexanone was reduced by about 52% and about 64% for Examples 5 and 5, respectively.

Example 4

A test was conducted with a mixture that had an initial concentration of about 1,000 ppmw of cyclohexanone in aniline. About 50 mL of aniline and about 0.05 mL cyclohexanone were mixed with one another. About 0.5 g of the cation exchange resin (Type 14) was added to the aniline and cyclohexanone mixture. The test conditions and results are shown in Table 4 below.

TABLE 4

| Example | Resin Type | Resin Quantity (g) | Bath Temp (° C.) | 15 min GC Results (ppmw) | 30 min GC Results (ppmw) | 60 min GC Results (ppmw) |
|---|---|---|---|---|---|---|
| Ex. 7 | 14 | 0.5 | 140 | 306 | 165 | 65 |

As shown in Table 4, when the aniline feed that contained about 1,000 ppmw of cyclohexanone was contacted with the cation exchange resin at a temperature of about 140° C. the concentration of cyclohexanone was reduced by about 93.5% after 60 minutes, which was a significant reduction.

Example 5

A test was conducted with a mixture that had a concentration of about 100 ppmw of cyclohexanone in aniline. About 50 mL aniline and 0.005 mL cyclohexanone were mixed with one another. About 0.5 g cation the exchange resin (Type 14) was added to the aniline and cyclohexanone mixture. The test conditions and results are shown in Table 5 below.

TABLE 5

| Example | Resin Type | Resin Quantity (g) | Bath Temp (° C.) | 15 min GC Results (ppmw) | 30 min GC Results (ppmw) | 60 min GC Results (ppmw) |
|---|---|---|---|---|---|---|
| Ex. 8 | 14 | 0.5 | 140 | 28 | 20 | 12 |

As shown in Table 5, when the dry aniline feed that contained 100 ppmw cyclohexanone was contacted with the cation exchange resin at a temperature of about 140° C. and the concentration of cyclohexanone was reduced by about 88% after 60 minutes, which was a significant reduction.

As shown in Tables 1-5, it was surprisingly and unexpectedly discovered that contacting aniline feeds that contain cyclohexanone with cation exchange resins at a temperature of about 110° C. to about 140° C. significantly reduce the concentration of cyclohexanone in the aniline feed. The degree or amount of cyclohexanone reduction can depend, at least in part, on the contact time with the resin, the initial concentration of the cyclohexanone, the type of resin, the temperature, and combinations of these process variables.

Embodiments described herein further relate to any one or more of the following paragraphs:

1. A method for purifying a crude aniline, comprising contacting a crude aniline comprising aniline, water, and cyclohexanone with a cation exchange resin to produce a cyclohexanone-lean product that contains less cyclohexanone than the crude aniline, wherein the cation exchange resin is a solid, a semi-solid, or a combination thereof.

2. The method according to paragraph 1, further comprising: hydrogenating nitrobenzene to produce the crude aniline; separating at least a portion of the water from the crude aniline to produce a dehydrated crude aniline; and contacting the dehydrated crude aniline with the cation exchange resin to produce the cyclohexanone-lean product.

3. The method according to paragraph 2, further comprising: cooling the dehydrated crude aniline to produce a cooled dehydrated crude aniline; contacting the cooled dehydrated crude aniline with the cation exchange resin to produce the cyclohexanone-lean product; and introducing the cyclohexanone-lean product to a separation column to produce a purified aniline product.

4. The method according to paragraph 3, wherein the crude aniline comprises about 85 wt % to about 99 wt % of aniline, about 1 wt % to about 15 wt % of water, and about 100 ppmw to about 15,000 ppmw of cyclohexanone, 5. The method according to paragraph 3 or 4, wherein the dehydrated crude aniline comprises about 98 wt % to about 99.9 wt % of aniline, less than 0.5 wt % of water, and about 100 ppmw to about 5,000 ppmw of cyclohexanone.

6. The method according to any one of paragraphs 3 to 5, wherein the purified aniline product comprises about 99 wt % to about 99.99 wt % of aniline, less than 0.5 wt % of water, and less than 100 ppmw of cyclohexanone.

7. The method according to any one of paragraphs 3 to 6, wherein the cooled dehydrated aniline is contacted with the cation exchange resin at a temperature of about 50° C. to about 150° C. for a time period of about 1 minute to about 15 minutes, and wherein the cyclohexanone-lean product contains at least 30% less cyclohexanone as compared to the crude aniline.

8. The method according to any one of paragraphs 3 to 6, wherein the cooled dehydrated aniline is contacted with the cation exchange resin at a temperature go about 50° C. to about 150° C. for a time period of less than 60 minutes, and wherein the cyclohexanone-lean product contains at least 50% less cyclohexanone as compared to the crude aniline.

9. The method according to paragraph 1, wherein the crude aniline is contacted with the cation exchange resin at a temperature of about 50° C. to about 150° C. for a time period of about 1 minute to about 15 minutes, and wherein the cyclohexanone-lean product contains at least 30% less cyclohexanone as compared to the crude aniline.

10. The method according to paragraph 1, wherein the crude aniline is contacted with the cation exchange resin at a temperature of about 50° C. to about 150° C. for a time period of about 1 minute to about 15 minutes, and wherein the cyclohexanone-lean product contains at least 40% less cyclohexanone as compared to the crude aniline.

11. The method according to paragraph 1, wherein the crude aniline is contacted with the cation exchange resin at a temperature of about 50° C. to about 150° C. for a time period of about 1 minute to about 15 minutes, and wherein the cyclohexanone-lean product contains at least 50% less cyclohexanone as compared to the crude aniline.

12. The method according to paragraph 1, wherein the crude aniline is contacted with the cation exchange resin at a temperature go about 50° C. to about 150° C. for a time period of less than 60 minutes, and wherein the cyclohexanone-lean product contains at least 50% less cyclohexanone as compared to the crude aniline.

13. The method according to paragraph 1, wherein the crude aniline is contacted with the cation exchange resin at a temperature go about 50° C. to about 150° C. for a time period of less than 60 minutes, and wherein the cyclohexanone-lean product contains at least 60% less cyclohexanone as compared to the crude aniline.

14. The method according to paragraph 1, wherein the crude aniline is contacted with the cation exchange resin at a temperature go about 50° C. to about 150° C. for a time period of less than 60 minutes, and wherein the cyclohexanone-lean product contains at least 70% less cyclohexanone as compared to the crude aniline.

15. The method according to any one of paragraphs 1 to 14, wherein the cation exchange resin comprises $H^+$ functional groups, sulfuric acid, $HSO_4^-$ functional groups, or any combination thereof.

16. The method according to any one of paragraphs 1 to 15, wherein the cation exchange resin is in the form of pellets, beads, granules, flakes, spheres, cubes, blocks, fibers, filaments, threads, or any mixture thereof.

17. The method according to any one of paragraphs 1 to 16, wherein the cation exchange resin comprises a polymer based on a cross-linked styrene divinylbenzene copolymer containing sulfuric acid and $HSO_4^-$ functional groups.

18. The method according to any one of paragraphs 1 to 17, wherein the cation exchange resin has an average pore diameter of about 100 Å to about 500 Å.

19. The method according to any one of paragraphs 1 to 18, wherein the cation exchange resin has a pore volume of about 0.1 mL/g to about 1 mL/g.

20. The method according to any one of paragraphs 1 to 19, wherein the cation exchange resin has a surface area of about 10 $m^2$/g to about 50 $m^2$/g.

21. The method according to any one of paragraph 1 to 20, wherein at least a portion of the crude aniline is contacted with the cation exchange resin at a rate of about 0.1 $m^3$ crude aniline per 1 $m^3$ of cation exchange resin per hour to about 30 $m^3$ of crude aniline per 1 $m^3$ of cation exchange resin per hour.

22. A method for purifying a crude aniline, comprising: hydrogenating an aromatic nitro compound to produce a crude aniline comprising about 85 wt % to about 99 wt % of aniline, about 1 wt % to about 15 wt % of water, and about 100 ppmw to about 15,000 ppmw of cyclohexanone; separating at least a portion of the water from the crude aniline to produce a dehydrated product comprising about 98 wt % or more of aniline, less than about 5,000 ppmw of water, and about 100 ppmw to about 5,000 ppmw of cyclohexanone; reacting a portion of the cyclohexanone with a portion of the aniline in the dehydrated product to produce a cyclohexanone-reduced product comprising less cyclohexanone than the dehydrated product; and contacting the cyclohexanone-reduced product at a temperature of about 50° C. to about 150° C. with a cation exchange resin to produce a cyclohexanone-lean product that comprises less cyclohexanone than the cyclohexanone-reduced product, wherein the cation exchange resin is solid, semi-solid, or a combination thereof.

23. The method according to paragraph 22, wherein the cyclohexanone-reduced product is contacted with the cation exchange resin for a time period of about 1 minute to about 15 minutes, and wherein the cyclohexanone-lean product contains at least 30% less cyclohexanone as compared to the cyclohexanone-reduced product.

24. The method according to paragraph 22 or 23, wherein the cation exchange resin comprises $H^+$ functional groups, sulfuric acid, $HSO_4^-$ functional groups, or any combination thereof.

25. The method according to any one of paragraphs 22 to 24, wherein the cation exchange resin comprises a polymer based on a cross-linked styrene divinylbenzene copolymer containing sulfuric acid, $HSO_4^-$, functional groups.

26. The method according to any one of paragraphs 22 to 25, wherein the portion of the cyclohexanone reacted with the portion of the aniline is reacted at a temperature of about 100° C. to about 170° C.

27. The method according to any one of paragraphs 22 to 26, wherein the cation exchange resin has an average pore diameter of about 100 Å to about 500 Å.

28. The method according to any one of paragraphs 22 to 27, wherein the cation exchange resin has a pore volume of about 0.1 mL/g to about 1 mL/g.

29. The method according to any one of paragraphs 22 to 28, wherein the cation exchange resin has a surface area of about 10 m$^2$/g to about 50 m$^2$/g.

30. A system for purifying a crude aniline, comprising: a hydrogenation reactor configured to hydrogenate an aromatic nitro compound to produce a crude aniline comprising aniline, water, and cyclohexanone; and a cation exchange unit configured to contact the crude aniline with a cation exchange resin to produce a cyclohexanone-lean product that contains less cyclohexanone than the crude aniline, wherein the cation exchange resin is solid, semi-solid, or a combination thereof.

31. The system according to paragraph 30, further comprising a dehydration unit configured to separate water from the crude aniline to produce a dehydrated crude aniline containing less water than the crude aniline, wherein the dehydration unit is located upstream of the cation exchange unit.

32. The system according to paragraph 30 or 31, further comprising a reactor configured to react a portion of the cyclohexanone in the dehydrated crude aniline to produce a cyclohexanone-reduced crude aniline, wherein the reactor is located upstream of the cation exchange unit and downstream of the dehydration unit.

33. The system according to any one of paragraphs 30 to 32, further comprising a separator configured to separate at least a portion of any impurities from the cyclohexanone-lean product to produce a purified aniline product.

Certain embodiments and features have been described using a set of numerical upper limits and a set of numerical lower limits. It should be appreciated that ranges including the combination of any two values, e.g., the combination of any lower value with any upper value, the combination of any two lower values, and/or the combination of any two upper values are contemplated unless otherwise indicated. Certain lower limits, upper limits and ranges appear in one or more claims below. All numerical values are "about" or "approximately" the indicated value, and take into account experimental error and variations that would be expected by a person having ordinary skill in the art.

Various terms have been defined above. To the extent a term used in a claim is not defined above, it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application and for all jurisdictions in which such incorporation is permitted.

While the foregoing is directed to embodiments of the present invention, other and further embodiments of the invention may be devised without departing from the basic scope thereof, and the scope thereof is determined by the claims that follow.

What is claimed is:

1. A method for purifying a crude aniline, comprising contacting a crude aniline comprising aniline, water, and cyclohexanone with a cation exchange resin to produce a cyclohexanone-lean product that contains less cyclohexanone than the crude aniline, wherein the cation exchange resin is a solid, a semi-solid, or a combination thereof.

2. The method of claim 1, further comprising:
hydrogenating nitrobenzene to produce the crude aniline;
separating at least a portion of the water from the crude aniline to produce a dehydrated crude aniline; and
contacting the dehydrated crude aniline with the cation exchange resin to produce the cyclohexanone-lean product.

3. The method of claim 2, further comprising:
cooling the dehydrated crude aniline to produce a cooled dehydrated crude aniline;
contacting the cooled dehydrated crude aniline with the cation exchange resin to produce the cyclohexanone-lean product; and
introducing the cyclohexanone-lean product to a separation column to produce a purified aniline product.

4. The method of claim 3, wherein the crude aniline comprises about 85 wt % to about 99 wt % of aniline, about 1 wt % to about 15 wt % of water, and about 100 ppmw to about 15,000 ppmw of cyclohexanone, wherein the dehydrated crude aniline comprises about 98 wt % to about 99.9 wt % of aniline, less than 0.5 wt % of water, and about 100 ppmw to about 5,000 ppmw of cyclohexanone, and wherein the purified aniline product comprises about 99 wt % to about 99.99 wt % of aniline, less than 0.5 wt % of water, and less than 100 ppmw of cyclohexanone.

5. The method of claim 1, wherein the crude aniline is contacted with the cation exchange resin at a temperature of about 50° C. to about 150° C. for a time period of about 1 minute to about 15 minutes, and wherein the cyclohexanone-lean product contains at least 30% less cyclohexanone as compared to the crude aniline.

6. The method of claim 1, wherein the crude aniline is contacted with the cation exchange resin at a temperature go about 50° C. to about 150° C. for a time period of less than 60 minutes, and wherein the cyclohexanone-lean product contains at least 50% less cyclohexanone as compared to the crude aniline.

7. The method of claim 1, wherein the cation exchange resin comprises $H^+$ functional groups, sulfuric acid, $HSO_4^-$ functional groups, or any combination thereof.

8. The method of claim 1, wherein the cation exchange resin is in the form of pellets, beads, granules, flakes, spheres, cubes, blocks, fibers, filaments, threads, or any mixture thereof.

9. The method of claim 1, wherein the cation exchange resin comprises a polymer based on a cross-linked styrene divinylbenzene copolymer containing sulfuric acid and $HSO_4^-$ functional groups.

10. The method of claim 1, wherein the cation exchange resin has an average pore diameter of about 100 Å to about 500 Å, a pore volume of about 0.1 mL/g to about 1 mL/g, and a surface area of about 10 m$^2$/g to about 50 m$^2$/g.

11. The method of claim 1, wherein at least a portion of the crude aniline is contacted with the cation exchange resin at a rate of about 0.1 m$^3$ crude aniline per 1 m$^3$ of cation exchange resin per hour to about 30 m$^3$ of crude aniline per 1 m$^3$ of cation exchange resin per hour.

12. A method for purifying a crude aniline, comprising:
hydrogenating an aromatic nitro compound to produce a crude aniline comprising about 85 wt % to about 99 wt % of aniline, about 1 wt % to about 15 wt % of water, and about 100 ppmw to about 15,000 ppmw of cyclohexanone;
separating at least a portion of the water from the crude aniline to produce a dehydrated product comprising about 98 wt % or more of aniline, less than about 5,000 ppmw of water, and about 100 ppmw to about 5,000 ppmw of cyclohexanone;
reacting a portion of the cyclohexanone with a portion of the aniline in the dehydrated product to produce a cyclohexanone-reduced product comprising less cyclohexanone than the dehydrated product; and
contacting the cyclohexanone-reduced product at a temperature of about 50° C. to about 150° C. with a cation exchange resin to produce a cyclohexanone-lean product that comprises less cyclohexanone than the cyclohexanone-reduced product, wherein the cation exchange resin is solid, semi-solid, or a combination thereof.

13. The method of claim 12, wherein the cyclohexanone-reduced product is contacted with the cation exchange resin for a time period of about 1 minute to about 15 minutes, and wherein the cyclohexanone-lean product contains at least 30% less cyclohexanone as compared to the cyclohexanone-reduced product.

14. The method of claim 13, wherein the cation exchange resin comprises H$^+$ functional groups, sulfuric acid, HSO$_4^-$ functional groups, or any combination thereof.

15. The method of claim 12, wherein the cation exchange resin comprises a polymer based on a cross-linked styrene divinylbenzene copolymer containing sulfuric acid, HSO$_4^-$, functional groups.

16. The method of claim 12, wherein the portion of the cyclohexanone reacted with the portion of the aniline is reacted at a temperature of about 100° C. to about 170° C.

17. A system for purifying a crude aniline, comprising:
a hydrogenation reactor configured to hydrogenate an aromatic nitro compound to produce a crude aniline comprising aniline, water, and cyclohexanone; and
a cation exchange unit configured to contact the crude aniline with a cation exchange resin to produce a cyclohexanone-lean product that contains less cyclohexanone than the crude aniline, wherein the cation exchange resin is solid, semi-solid, or a combination thereof.

18. The system of claim 17, further comprising a dehydration unit configured to separate water from the crude aniline to produce a dehydrated crude aniline containing less water than the crude aniline, wherein the dehydration unit is located upstream of the cation exchange unit.

19. The system of claim 18, further comprising a reactor configured to react a portion of the cyclohexanone in the dehydrated crude aniline to produce a cyclohexanone-reduced crude aniline, wherein the reactor is located upstream of the cation exchange unit and downstream of the dehydration unit.

20. The system of claim 19, further comprising a separator configured to separate at least a portion of any impurities from the cyclohexanone-lean product to produce a purified aniline product.

* * * * *